(12) United States Patent
Nishigaya et al.

(10) Patent No.: US 8,043,580 B2
(45) Date of Patent: Oct. 25, 2011

(54) TESTING DEVICE

(75) Inventors: Toshiomi Nishigaya, Yuki (JP); Ryuichi Endo, Yuki (JP)

(73) Assignee: Nissui Pharmaceutical Co., Ltd., Tokyo (JP)

( * ) Notice: Subject to any disclaimer, the term of this patent is extended or adjusted under 35 U.S.C. 154(b) by 757 days.

(21) Appl. No.: 12/089,925

(22) PCT Filed: Oct. 12, 2006

(86) PCT No.: PCT/JP2006/320403
§ 371 (c)(1),
(2), (4) Date: Apr. 11, 2008

(87) PCT Pub. No.: WO2007/043619
PCT Pub. Date: Apr. 19, 2007

(65) Prior Publication Data
US 2010/0047131 A1    Feb. 25, 2010

(30) Foreign Application Priority Data
Oct. 13, 2005  (JP) .................. 2005-298697

(51) Int. Cl.
| | |
|---|---|
| G01N 21/75 | (2006.01) |
| G01N 31/22 | (2006.01) |
| G01N 33/52 | (2006.01) |
| B01L 3/00 | (2006.01) |
| G01N 21/00 | (2006.01) |
| G01F 25/00 | (2006.01) |
| C12M 3/00 | (2006.01) |

(52) U.S. Cl. .......... 422/400; 422/81; 422/402; 422/412; 422/417; 422/430; 435/288.5; 435/287.2; 73/1.72; 73/1.73; 73/1.02

(58) Field of Classification Search .................. None
See application file for complete search history.

(56) References Cited

U.S. PATENT DOCUMENTS
5,609,828 A    3/1997   O'Bear et al.
(Continued)

FOREIGN PATENT DOCUMENTS
| JP | 7 506257 | 7/1995 |
| JP | 7-260774 | 10/1995 |
| JP | 9-196852 | 7/1997 |

(Continued)

OTHER PUBLICATIONS

Office Action issued Mar. 28, 2011, in Europe Patent Application No. 06 811 691.2-1270.

Primary Examiner — Brian J Sines
Assistant Examiner — Jennifer Wecker
(74) Attorney, Agent, or Firm — Oblon, Spivak, McClelland, Maier & Neustadt, L.L.P.

(57) ABSTRACT

A testing device is provided which is able to distribute a liquid sample to a plurality of reaction sections by a simple operation without using a tip dispenser, and also achieves individually independent reaction systems without causing reaction sections to be in communication with each other due to a liquid sample. The testing device has a transparent molded body which includes: a storage chamber for injecting/holding a liquid sample; a reaction chamber for causing a reaction of the sample; a receiving chamber for sucking and receiving the sample, with the storage chamber and the reaction chamber being in communication with each other via a distributing flow path, and the reaction chamber and the receiving chamber being in communication with each other via a sucking flow path; and a liquid reservoir between the reaction chamber and the receiving chamber.

24 Claims, 9 Drawing Sheets

U.S. PATENT DOCUMENTS

| | | | |
|---|---|---|---|
| 6,184,029 B1 * | 2/2001 | Wilding et al. | 435/287.1 |
| 7,473,397 B2 * | 1/2009 | Griffin et al. | 422/57 |
| 2002/0055167 A1 * | 5/2002 | Pourahmadi et al. | 435/287.2 |
| 2002/0068357 A1 * | 6/2002 | Mathies et al. | 435/287.2 |
| 2004/0099310 A1 * | 5/2004 | Andersson | 137/240 |
| 2005/0106066 A1 | 5/2005 | Saltsman et al. | |
| 2005/0148091 A1 * | 7/2005 | Kitaguchi et al. | 436/164 |
| 2006/0090800 A1 | 5/2006 | Banerjee et al. | |

FOREIGN PATENT DOCUMENTS

| | | |
|---|---|---|
| JP | 2000 55911 | 2/2000 |
| JP | 2002 503336 | 1/2002 |
| JP | 03 536058 | 12/2003 |
| JP | 2005 140666 | 6/2005 |
| WO | 03 093836 | 11/2003 |
| WO | 2004 029221 | 4/2004 |

* cited by examiner (A)

(B)

SAMPLE

TESTING DEVICE

TECHNICAL FIELD

The present invention relates to a testing device which is suitable for analyzing a liquid sample.

BACKGROUND ART

A microplate or the like is a widely known testing device having a plurality of reaction sections, and in using the microplate, usually, a sample is distributed to each of the reaction sections by dispensing the sample using a tip or the like. In recent years, more compact testing devices have been developed, which provide a system for distributing a liquid to each reaction section by using centrifugal force (see Japanese Patent Application Laid-Open Publication No. 7-260774) or forming a negative pressure in the device (see Japanese Patent Application Laid-Open Publication No. 9-196852), without using a tip or the like.

The system which uses the formation of a negative pressure for distribution provides an advantage that a dispensation is easier and takes less time as compared to the method using a tip, but in the system, a sample is left in flow paths through which the sample is distributed to each reaction section, and the reaction sections get in communication with each other due to the left sample, thereby it was impossible to establish completely independent systems.

In addition, the system which uses the formation of a negative pressure for distribution requires a special pressure reduction apparatus (container) to maintain the entire device under a negative pressure, and the system which uses centrifugal force also requires a centrifugal apparatus, and both of the apparatuses are complicated in operation.

DISCLOSURE OF THE INVENTION

Problems to be Solved by the Invention

The present invention relates to provide a testing device which is able to distribute a liquid sample to a plurality of reaction sections by a simple operation without using a tip for dispensing the sample to the reaction sections, and also establish individually independent reaction systems without causing the reaction sections to be in communication with each other due to the liquid sample.

Means for Solving the Problems

In other words, the present invention relates to a testing device which includes a transparent molded body having: a storage chamber for injecting/holding a liquid sample; a reaction chamber for causing a reaction of the sample; a receiving chamber for sucking and receiving the sample, with the storage chamber and the reaction chamber being in communication with each other via a distributing flow path, and the reaction chamber and the receiving chamber being in communication with each other via a sucking flow path; and a liquid reservoir between the reaction chamber and the receiving chamber.

Effects of the Invention

According to a testing device of the present invention, a liquid sample is ensured to be distributed to a plurality of reaction sections by a simple operation, and also individually independent reaction systems can be established without causing the reaction sections to be in communication with each other due to the liquid sample. Therefore, a testing device of the present invention is useful as a device which carries out bacteriological tests for antimicrobial susceptibility and identification of a microbe, biochemistry and immunologic tests for measurement of an antibody and measurement of an enzyme activity, and optical measurements which are used in genetic tests for DNA and RNA detection (absorption measurement, fluorescence measurement, luminescence measurement, and the like), for example, in a simple manner.

Figure 1:
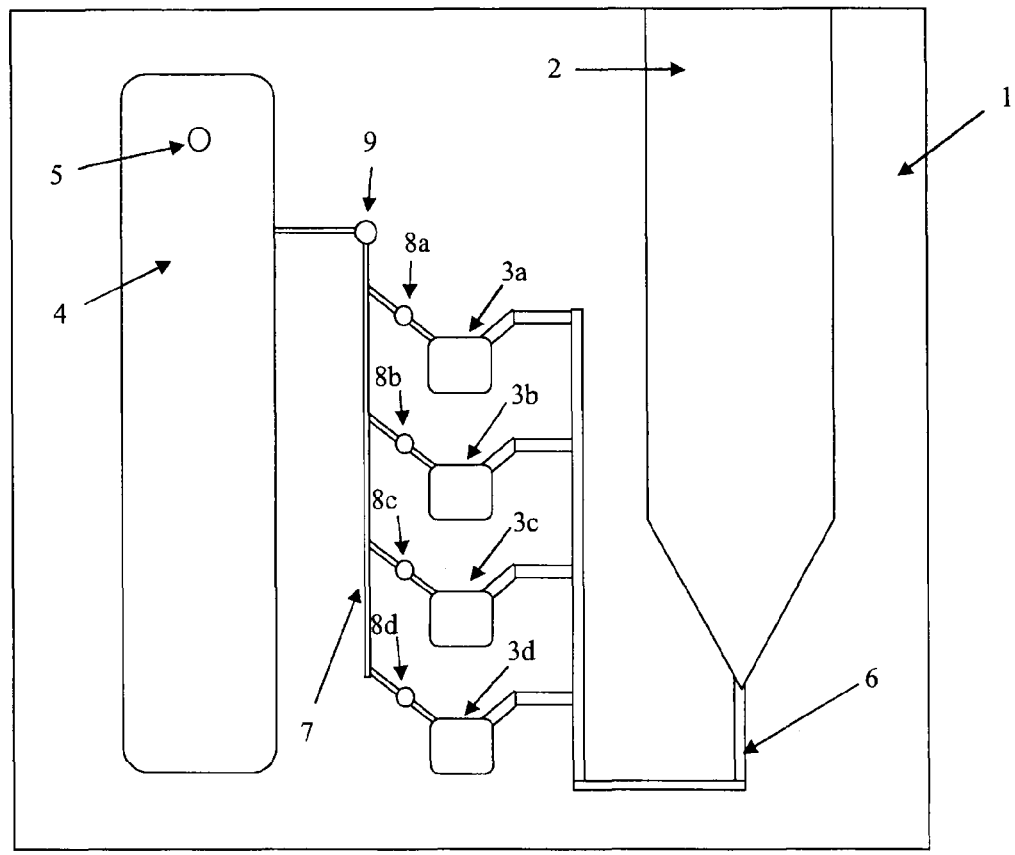
FIG. 1 is a plan view showing a testing device according to the present invention.

DESCRIPTION OF SYMBOLS 1 substrate
2 storage chamber
3, 3a to 3d reaction chamber
4 receiving chamber
5 sucking port
6 distributing flow path
7 sucking flow path
8, 8a to 8d liquid reservoir
9 liquid reservoir
10 film or resin plate
11 receiving chamber
12 sucking port
13 liquid reservoir
14 liquid reservoir
15 through flow path
16 storage chamber
17 filtering flow path
18 air tank
19 liquid reservoir
20 connecting flow path
21 receiving chamber

BEST MODE FOR CARRYING OUT THE INVENTION

A testing device of the present invention includes a transparent molded body having: a storage chamber for injecting/ holding a liquid sample; a reaction chamber for causing a reaction of the sample; a receiving chamber for sucking and receiving the reacted sample, with the storage chamber and the reaction chamber being in communication with each other via a distributing flow path and the reaction chamber and the receiving chamber being in communication with each other via a sucking flow path; and a liquid reservoir between the reaction chamber and the receiving chamber. The device is configured to suck a sample using liquid sucking means from a sucking port which is provided in the receiving chamber so that the liquid sample is dispensed from the storage chamber to the reaction chamber.

Now, an embodiment of the present invention will be explained below by way of FIGS. 1 to 7.

In the figures, reference numeral 1 denotes a substrate, reference numerals 2, 16 denote storage chambers, reference numerals 3, 3a to 3d denote reaction chambers, reference numerals 4, 11 and 21 denote receiving chambers, reference numeral 5 denotes a sucking port, reference numeral 6 denotes a distributing flow path, reference numeral 7 denotes a sucking flow path, reference numerals 8, 8a to 8d, 9, 13, 14 and 19 denote liquid reservoirs, reference numeral 10 denotes a film or resin plate, reference numeral 15 denotes a through flow path, reference numeral 17 denotes a filtering flow path, reference numeral 18 denotes an air tank, and reference numeral 20 denotes a connecting flow path.

FIG. 1 is a plan view showing a basic structure of a testing device according to the present invention.

The substrate 1 is a transparent structure for forming a molded body which fixedly supports a storage chamber, a reaction chamber, a distributing flow path, and a sucking flow path thereon, but as far as the reaction chamber is configured to allow an optical measurement from outside, the entire substrate 1 may not be necessarily transparent.

The substrate may be formed of any material, without limitation, to which an optical measurement and a temperature control can be carried out, including: inorganic materials such as metal, glass, quartz glass, alumina, sapphire, forsterite, silicon carbide, silicon oxide, and silicon nitride; or organic materials such as polyethylene, ethylene vinyl acetate copolymer resin, polypropylene, polystyrene (PS), AS resin, ABS resin, methacryl resin, polyvinyl chloride, polyamide, polycarbonate (PC), polyethylene terephthalate, polybutylene terephthalate, phenolic resin, urea resin, epoxy resin, melamine resin, cycloolefin resin, and acrylic resin (PMMA).

The molded body (substrate) may be formed into any shape without limitation, but is preferably formed into a plate shape so that a biochemical reaction can be directly detected in the reaction chamber from outside.

Figure 2:
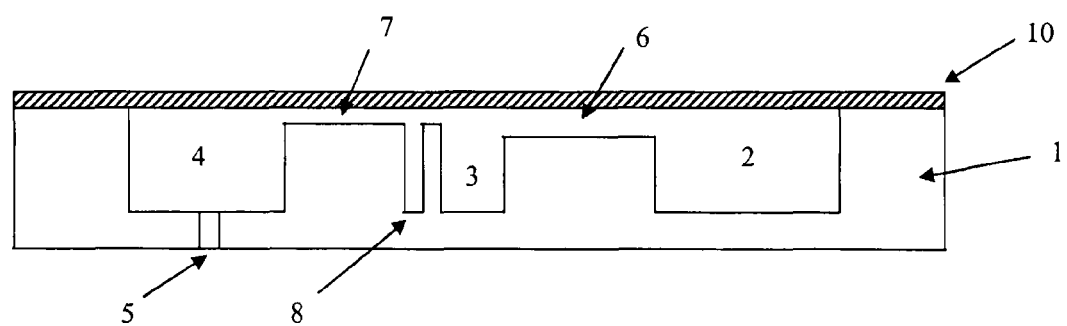
FIG. 2 is a side view showing the testing device of FIG. 1.

The molded body (substrate) may not be necessarily integrally formed, and, as shown in FIG. 2 (side view), may be formed by covering a plate substrate having grooves formed therein with a transparent film or a resin plate, for example. The grooves correspond to the storage chamber, the reaction chamber, the distributing flow path, the sucking flow path, and the like. Herein, the film or the resin plate may be of organic materials such as silicone resin, polyethylene, ethylene vinyl acetate copolymer resin, polyvinyl chlorides, polyurethane, polyvinyl butyral, polyvinyl alcohol, vinyl acetate resin, phenolic resin, urea resin, epoxy resin, and melamine resin, but the material is not limited to these. Preferred materials include a polyolefin sheet, a polyethylene sheet, and a polypropylene sheet.

The storage chamber 2 is a section for injecting/holding a liquid sample, and is open to the outside through an injection port for injecting a liquid sample formed therein. The storage chamber may be formed into any shape without limitation, but is preferably formed in a shape which tapers toward the bottom thereof toward a distributing flow path. As may be needed, a plurality of storage chambers may be provided (see FIG. 6), and also a flow path (filtering flow path 17) which functions as a filter may be provided between the storage chambers (see FIG. 6).

The sample liquid may be any type including, without limitation, liquid samples such as blood, cerebrospinal fluids and urine, which are used in the clinical medicine and pharmacology field; samples in the environment and food industry fields such as environmental water, drinking water, and suspensions of ground food; samples in fields of microbes and cells such as microbes (e.g., bacteria, fungi), bacteria suspensions, and liquid cultures.

After injected in the storage chamber 2, the liquid sample is sucked through the sucking port 5 formed in the receiving chamber 4 using an appropriate liquid sucking means such as a syringe pump or a diaphragm pump to be dispensed to the reaction chambers 3a to 3d via the distributing flow path 6. The distributing flow path 6 is branched, before reaching each reaction chamber, to be guided to each reaction chamber, thereby the time required for dispensing the sample to each reaction chamber can be reduced (see FIGS. 5 to 7).

The reaction chambers 3a to 3d may be filled with a reagent for example in advance. The reagent may be an antigen, an antibody, a medium ingredient, a substrate, and nucleic acid, for example. The number of the reaction chambers is not limited, and may be 48, 64, 80, and 96 although the size of a substrate limits the number (see FIG. 7).

A measurement of a reaction result is carried out by measuring the reaction products in the reaction chambers using optical means.

Between the reaction chambers 3a to 3d and the receiving chamber 4, there are provided the liquid reservoirs 8a to 8d that function as a resistance so that the sample is distributed to all of the reaction chambers before the liquid reservoirs are filled up with the sample, which ensures that the sample is distributed to the plurality of reaction chambers.

The liquid reservoirs may be configured in any way as far as the liquid reservoirs are not filled up with the sample before the sample is distributed to all of the reaction chambers, and for example, the widths or depths of the sucking flow path and the distributing flow path may be controlled so that the sucking flow path has a cross-section area smaller than that of the distributing flow path.

Figure 3:
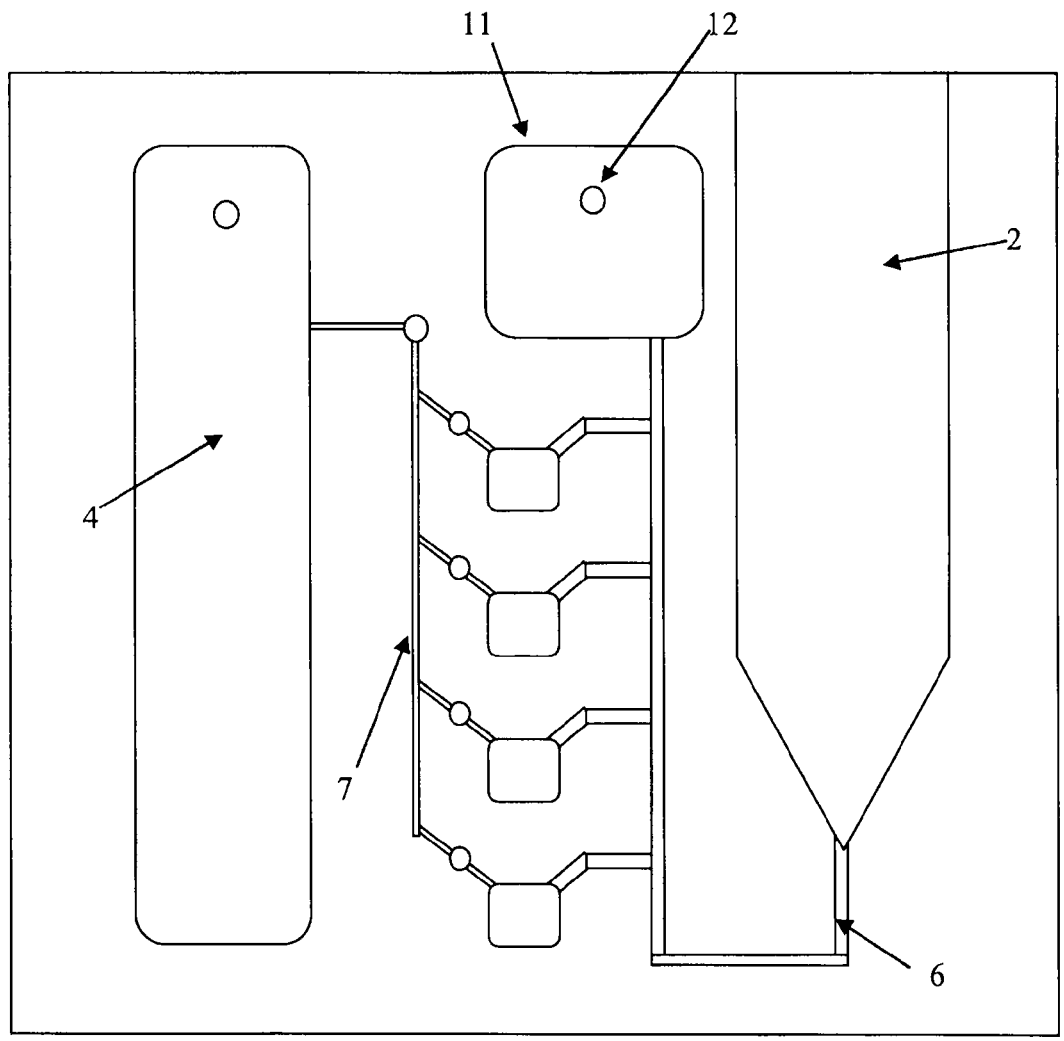
FIG. 3 is a plan view showing a testing device according to the present invention (which is provided with a second receiving chamber downstream of a distributing flow path)
Figure 7:
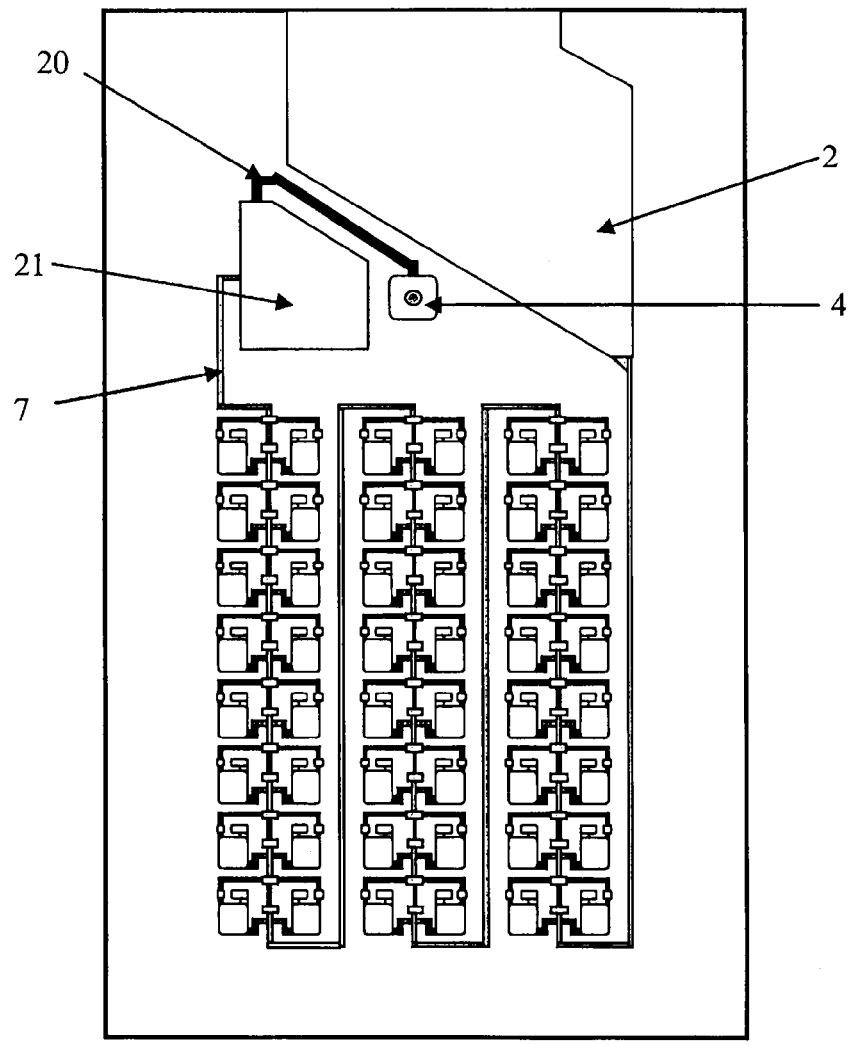
FIG. 7 is a plan view showing a testing device according to the present invention (in which a distributing flow path is branched into two to have 48 reaction chambers in total)
Figure 7:
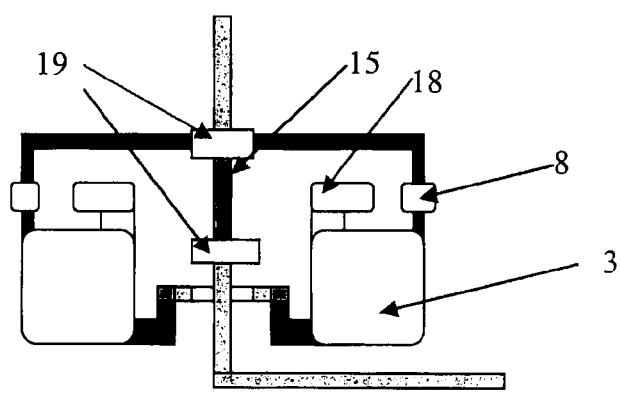

Moreover, two or more receiving chambers may be provided as may be needed (see FIG. 3 and FIG. 7).

FIG. 3 shows a device which is provided with a new second receiving chamber 11 having a sucking port 12 downstream of the distributing flow path 6. After the liquid sample is distributed to each reaction chamber as described above, a suction of the liquid sample into the sucking port 12 provided in the receiving chamber 11 allows a recovery of the liquid sample which is left in the distributing flow path 6 into the receiving chamber 11. This prevents each reaction chamber from being in communication with due to the left liquid sample, which enables the establishment of individually independent reaction systems.

Figure 4:
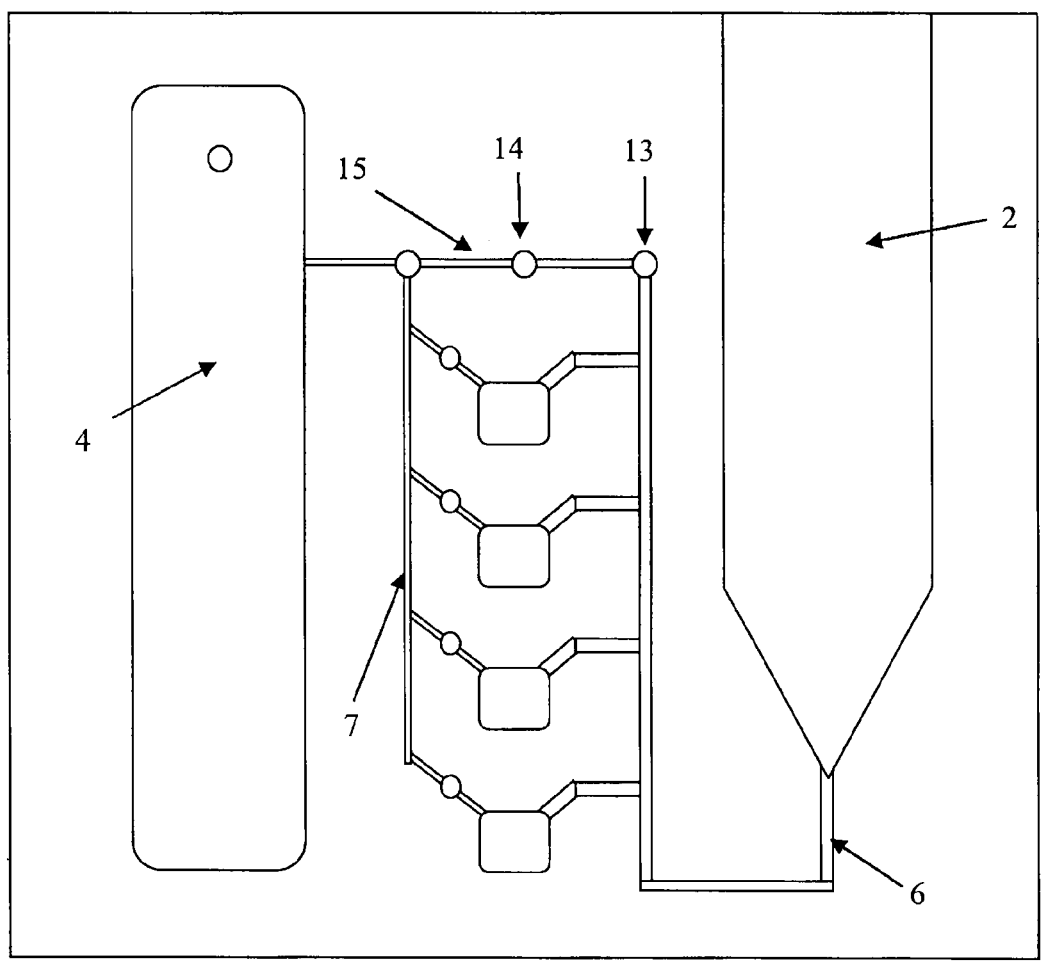
FIG. 4 is a plan view showing a testing device according to the present invention (which is provided with a new through path connecting a distributing flow path and a sucking flow path)

FIG. 4 shows a device which is provided with a new through flow path 15 connecting between the distributing flow path 6 and the sucking flow path 7. In this case, after a sample is distributed to each reaction chamber by a suction of the sample through the sucking port 5, the suction is continued, and the liquid sample left in the distributing flow path 6 is introduced into the receiving chamber 4 via the through flow path 15. The through flow path 15 desirably has a cross-section area larger than that of the sucking flow path 7 and smaller than that of the distributing flow path 6. Specifically, the through flow path 15 is provided with liquid reservoirs (13, 14) for example to control the cross-section area of the through flow path 15, so that the path 15 is designed to selectively pass through. In this way, a new through flow path connecting between the distributing flow path and the sucking flow path enables the distribution of a liquid sample to the reaction chambers and the disposal of the liquid sample left in the distributing flow path to be carried out by a single suction operation.

Figure 5:
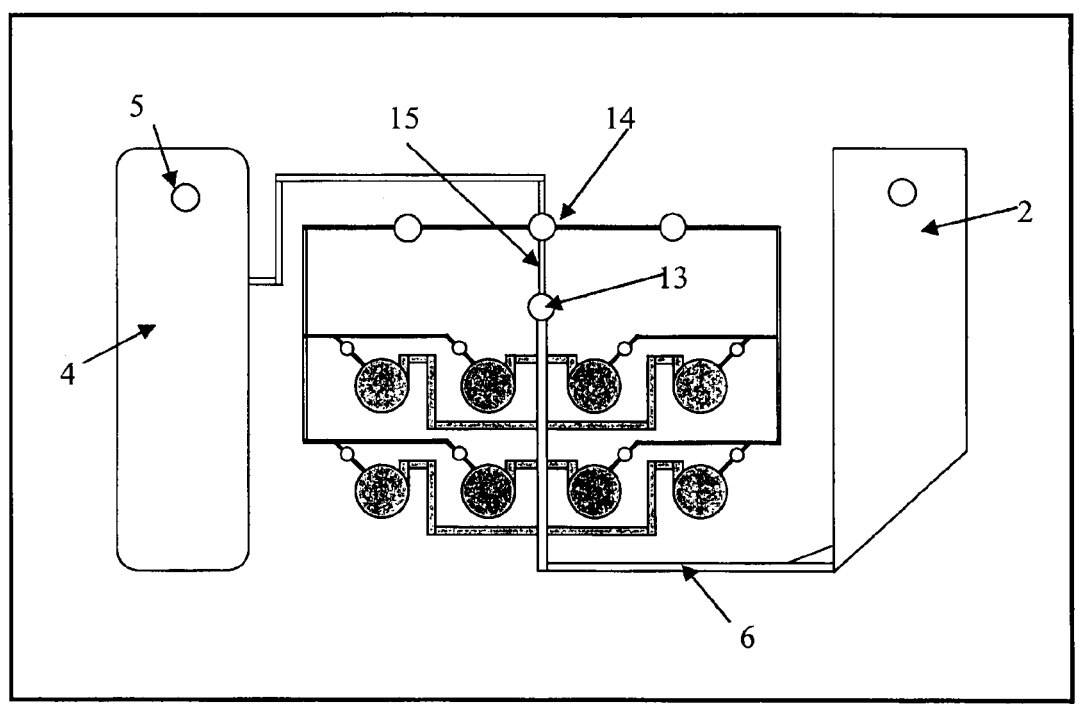
FIG. 5 is a plan view showing a testing device according to the present invention (in which a distributing flow path is branched)
Figure 6:
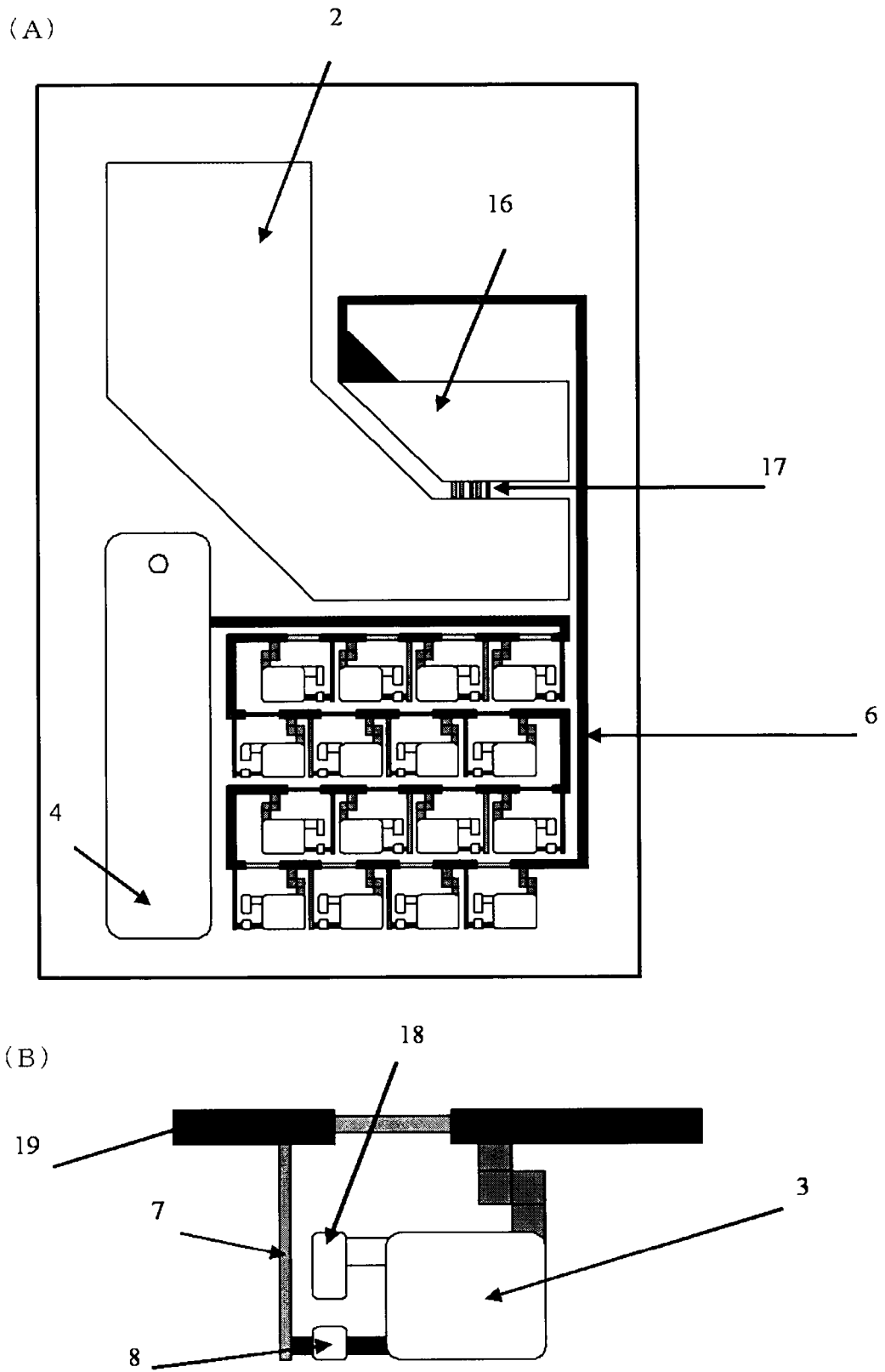
FIG. 6 is a plan view showing a testing device according to the present invention (which is provided with two storage chambers and a filtering flow path between the storage chambers)

FIG. 5 shows a device in which the distributing flow path 6 is branched so that a sample can be simultaneously distributed to a plurality of reaction chambers.

When a sample is sucked through the sucking port 5 provided in the receiving chamber 4, the sample is distributed to each of the eight reaction chambers through the distributing flow path 6. A further suction causes the sample in the distributing flow path to be introduced in the receiving chamber 4 via the central through flow path 15.

According to the present device, the branched distributing flow path enables a reduction of the time for distribution. Also, the branched distributing flow path enables a reduction of the distance between the reaction chambers, resulting in the size reduction of the entire device.

FIG. 6(A) shows a device which is provided with two storage chambers and a filtering flow path 17 between the storage chambers.

After poured into a first storage chamber 2, a sample is introduced into a second storage chamber 16 via the filtering flow path 17 by suction. Then, the sample is distributed to 16 reaction chambers in series via the distributing flow path 6. The two storage chambers having one or more filtering flow path therebetween enables a filtering of contaminants in a sample, which prevents any clogging of paths and failure of distribution.

FIG. 6(B) is an enlarged view showing a reaction chamber of the device, and reference numeral 18 denotes an air tank which supplies oxygen to the reaction chamber, and reference numeral 19 denotes a liquid reservoir (which controls the width of the path). The air tank 18 is configured not to be filled with a liquid sample, thereby an air layer is left and oxygen can be supplied after a sample is distributed, which enables the execution of a culture examination that requires oxygen.

FIG. 7(A) shows a device having three columns of eight stages of a distribution system in which a distributing flow path 6 is branched into two to arrange a pair of reaction chambers thereto, so that 48 reaction chambers are provided in total. FIG. 7(B) is an enlarged view showing a reaction chamber of the device.

In the present device, the through flow path 15 and the liquid reservoirs are provided for each distribution system having a pair of reaction chambers, which ensures the distribution of a sample to each reaction chamber.

Figure 8:
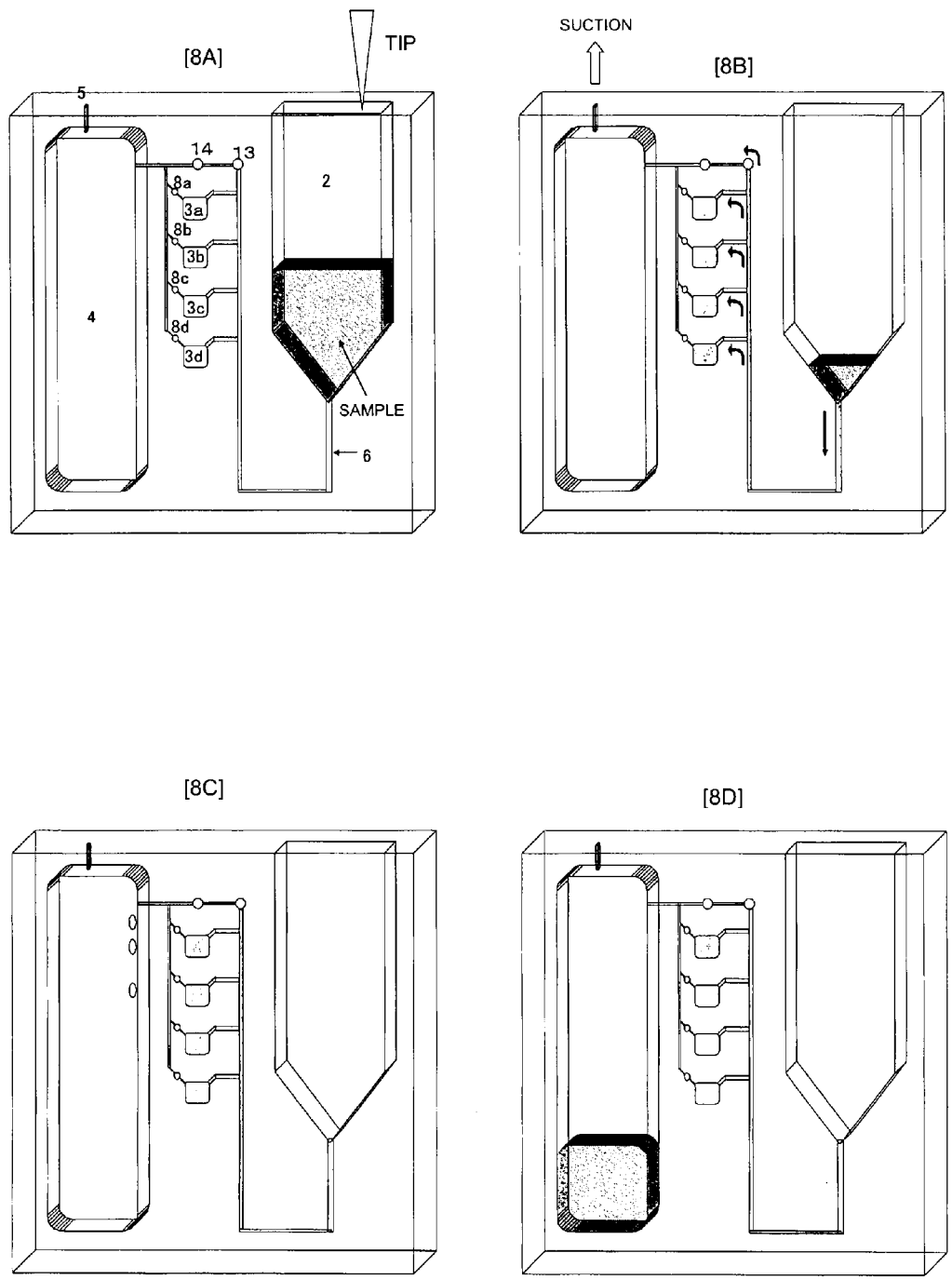
FIG. 8 is a view showing a distributing procedure of a sample using a testing device according to the present invention.

FIG. 8 shows a procedure for distributing a sample by using a testing device according to the present invention, by way of an example of a testing device which is provided a new through flow path connecting between a distributing flow path and a sucking flow path.

That is, after injected into the storage chamber 2 from an injection port, a sample liquid (FIG. 8A) is sucked through the sucking port 5 provided in the receiving chamber 4 by liquid sucking means, and reaches the reaction chambers 3a to 3d via the distributing flow path 6 to be distributed (FIG. 8B). At this point of time, the sample liquid is temporarily stopped before it reaches the liquid reservoirs 8a to 8d because of the resistance, and also stopped before it reaches the liquid reservoir 14. A further suction allows the path having the liquid reservoir 14 to pass through (FIG. 8C). A further suction causes the sample in the distributing flow path to be replaced with air so as to make the reaction chambers independent from each other (FIG. 8D). Finally, the top of the device is sealed to form a closed system.

EXAMPLES

Example 1

Figure 9:
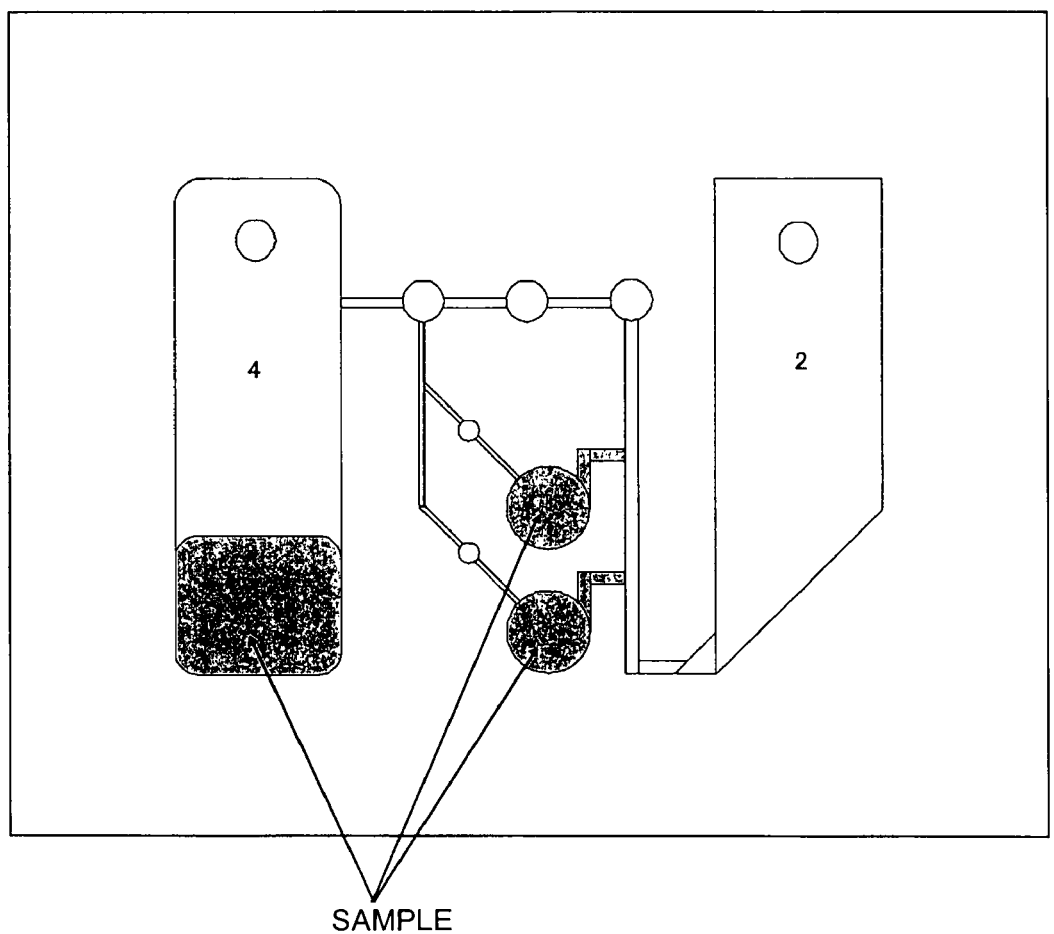
FIG. 9 is a view showing a state with a liquid being dispensed using a testing device according to the present invention.

The testing device shown in FIG. 9 was used, and after purified water 100 μL was dispensed into an injection port and a syringe pump was attached to a sucking port, a suction was started. It was confirmed that the purified water reached to all of the reaction chambers as shown in FIG. 9, and that a dispensation to independent systems of reaction could be achieved.

Example 2

Culture Examination (1)

In the reaction chamber of the device shown in FIG. 7, a fluorescent substrate of 4-Methylumbelliferyl-β-D-galactoside 10 μg/well was dried and immobilized. Bacterial strain (*Escherichia coli* ATCC 25922) which had been pre-cultured on a non-selective agar medium was suspended in sterile saline, and the obtained bacterial suspension was dispensed in a specimen tank, which was sucked through a sucking port to be distributed to each reaction well. The device was incubated using a commercially available plate reader, and the fluorescence (excitation wavelength: 360 nm, fluorescence(emission) wavelength: 450 nm) of each well was measured every hour.

Figure 10:
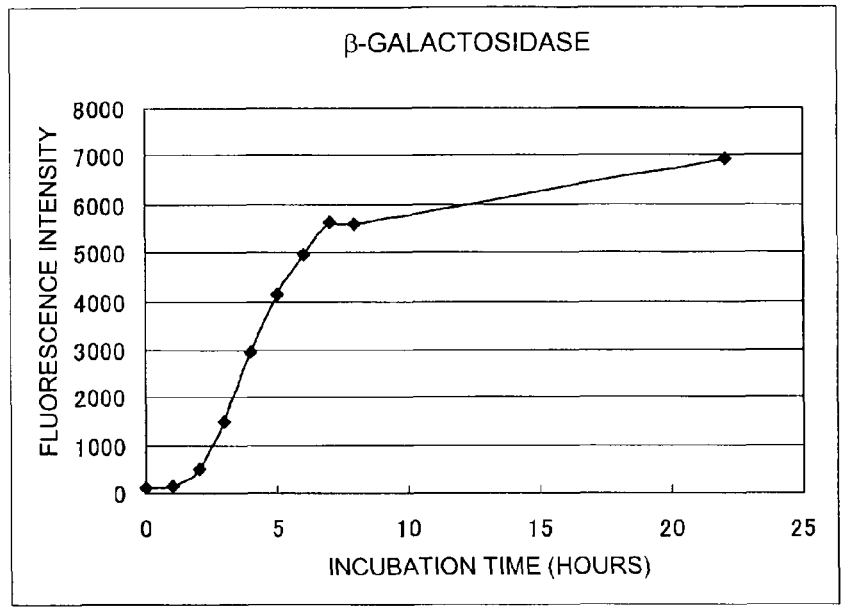
FIG. 10 is a graph showing a measurement result of a culture examination (β-galactosidase)

As shown in FIG. 10, it was identified that, as the incubation time passed, a fluorescence intensity was increased and that this strain had β-galactosidase.

Example 3

Culture Examination (2)

In the reaction chamber of the device shown in FIG. 7, WST-1 (2-(4-Indophenyl)-3-(4-nitrophenyl)-5-(2,4-disulfophenyl)-2H-tetrazolium, monosodium salt) 130 to 200 μg/mL, and amikacin (AMK) 0.125 μg/mL, 0.25 μg/mL, 0.5 μg/mL, 1 μg/mL, 2 μg/mL, 4 μg/mL, 8 μg/mL, 16 μg/mL, and 32 μg/mL were dried and immobilized. Bacterial strain (*E. coli* ATCC 25922) which had been pre-cultured on a non-selective agar medium was suspended in sterile saline, and the bacterial suspension was diluted by MHB (Mueller Hinton Broth) and dispensed in a specimen tank, which was sucked through a sucking port to be distributed to each reaction well. The device was incubated using a commercially available plate reader, and an absorbance at 440 nm of each well was measured every thirty minutes.

Figure 11:
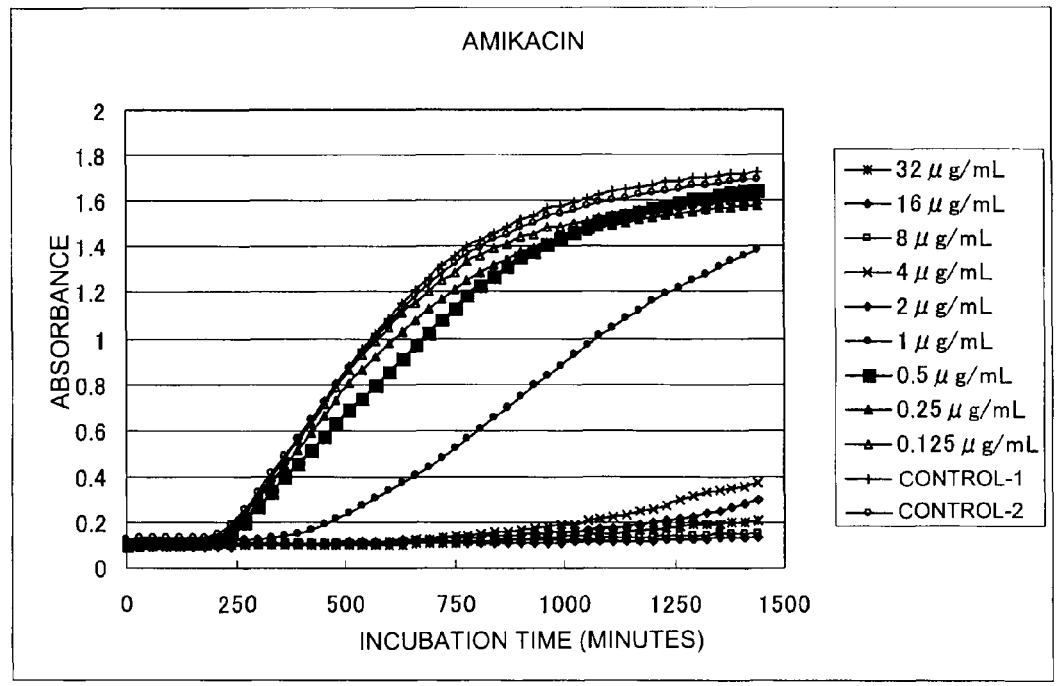
FIG. 11 is a graph showing a measurement result of a culture examination (minimum inhibitory concentration, MIC).

As shown in FIG. 11, it was identified that, as the bacterial growth was advanced, an absorbance was increased, and the minimum inhibitory concentration (MIC) could be obtained with analyzing the difference between the growth curves due to antimicrobial concentrations.

The invention claimed is:
1. A testing device comprising:
  a transparent molded body comprising:
    a storage chamber for injecting/holding a liquid sample;
    a plurality of reaction chambers for causing a reaction of
      the liquid sample, wherein the storage chamber and the reaction chambers are in communication with each other via a distributing flow path;

a receiving chamber for receiving the liquid sample, wherein the reaction chambers and the receiving chamber are in communication with each other via a sucking flow path;

a sucking port located in the receiving chamber for sucking the liquid sample, wherein the liquid sample is distributed from the storage chamber to the reaction chambers via the distributing flow path by a suction provided by the sucking port;

a liquid reservoir for each of the reaction chambers and located between each of the reaction chambers and the receiving chamber; and a through flow path connecting the distributing flow path and the sucking flow path, wherein the liquid sample remaining in the distributing flow path is replaced by air and introduced into the receiving chamber via the through flow path by a further suction provided by the sucking port so as to make the reaction chambers independent from each other.

2. The testing device according to claim 1, which further comprises:

a second receiving chamber having a second sucking port and being in communication with the distributing flow path, wherein the liquid sample remaining in the distributing flow path is replaced by air and introduced into the second receiving chamber by a second suction provided by the second sucking port so as to make the reaction chambers independent from each other.

3. The testing device according to claim 1, which further comprises:

an air tank that is attached, and supplies oxygen, to each of the reaction chambers.

4. The testing device according to claim 1, wherein the distributing flow path is branched prior to reaching the reaction chambers.

5. The testing device according to claim 1, wherein the transparent molded body is obtained by covering a plate substrate having a groove formed therein with a film or a resin plate, wherein one or more of the plate substrate, the film and the resin plate are transparent.

6. The testing device according to claim 5, wherein the film or the resin plate is composed of an organic material selected from the group consisting of a polyolefin resin, a polyethylene resin, a polypropylene resin, a silicon resin, an ethylene vinyl acetate copolymer resin, a polyvinyl chloride resin, a polyurethane resin, a polyvinyl butyral resin, a polyvinyl alcohol resin, a vinyl acetate resin, a phenolic resin, a urea resin, an epoxy resin, and a melamine resin.

7. The testing device according to claim 5, wherein the film or the resin plate is composed of an organic material selected from the group consisting of a polyolefin resin, a polyethylene resin, a polypropylene resin.

8. The testing device according to claim 5, wherein the plate substrate is composed of an organic material selected from the group consisting of a polyethylene resin, a polypropylene resin, an ethylene vinyl acetate copolymer resin, a polystyrene resin, an AS resin, an ABS resin, a methacryl resin, a polyvinyl chloride resin, a polyamide resin, a polycarbonate resin, a polyethylene terephthalate resin, a polybutylene terephthalate resin, a phenolic resin, a urea resin, an epoxy resin, a melamine resin, a cycloolefin resin, and an acrylic resin.

9. A testing device comprising:

a transparent molded body comprising:

a storage chamber for injecting/holding a liquid sample;

a plurality of reaction chambers for causing a reaction of the liquid sample, wherein the storage chamber and the reaction chambers are in communication with each other via a distributing flow path;

a receiving chamber for receiving the liquid sample, wherein the reaction chambers and the receiving chamber are in communication with each other via a sucking flow path;

a sucking port located in the receiving chamber for sucking the liquid sample, wherein the liquid sample is distributed from the storage chamber to the reaction chambers via the distributing flow path by a suction provided by the sucking port;

a liquid reservoir located between the reaction chambers and the receiving chamber; and a second receiving chamber having a second sucking port and being in communication with the distributing flow path, wherein the liquid sample remaining in the distributing flow path is replaced by air and introduced into the second receiving chamber by a second suction provided by the second sucking port so as to make the reaction chambers independent from each other.

10. The testing device according to claim 9, which further comprises:

a through flow path connecting the distributing flow path and the sucking flow path, wherein the liquid sample remaining in the distributing flow path is replaced by air and introduced into the receiving chamber via the through flow path by a further suction provided by the sucking port so as to make the reaction chambers independent from each other.

11. The testing device according to claim 9, which further comprises:

an air tank that is attached, and supplies oxygen, to each of the reaction chambers.

12. The testing device according to claim 9, wherein the distributing flow path is branched prior to reaching the reaction chambers.

13. The testing device according to claim 9, wherein the transparent molded body is obtained by covering a plate substrate having a groove formed therein with a film or a resin plate, wherein one or more of the plate substrate, the film and the resin plate are transparent.

14. The testing device according to claim 13, wherein the film or the resin plate is composed of an organic material selected from the group consisting of a polyolefin resin, a polyethylene resin, a polypropylene resin, a silicon resin, an ethylene vinyl acetate copolymer resin, a polyvinyl chloride resin, a polyurethane resin, a polyvinyl butyral resin, a polyvinyl alcohol resin, a vinyl acetate resin, a phenolic resin, a urea resin, an epoxy resin, and a melamine resin.

15. The testing device according to claim 13, wherein the film or the resin plate is composed of an organic material selected from the group consisting of a polyolefin resin, a polyethylene resin, a polypropylene resin.

16. The testing device according to claim 13, wherein the plate substrate is composed of an organic material selected from the group consisting of a polyethylene resin, a polypropylene resin, an ethylene vinyl acetate copolymer resin, a polystyrene resin, an AS resin, an ABS resin, a methacryl resin, a polyvinyl chloride resin, a polyamide resin, a polycarbonate resin, a polyethylene terephthalate resin, a polybutylene terephthalate resin, a phenolic resin, a urea resin, an epoxy resin, a melamine resin, a cycloolefin resin, and an acrylic resin.

17. A testing device comprising:
a transparent molded body comprising:
- a storage chamber for injecting/holding a liquid sample;
- a plurality of reaction chambers for causing a reaction of the liquid sample, wherein the storage chamber and the reaction chambers are in communication with each other via a distributing flow path;
- a receiving chamber for receiving the liquid sample, wherein the reaction chambers and the receiving chamber are in communication with each other via a sucking flow path;
- a sucking port located in the receiving chamber for sucking the liquid sample, wherein the liquid sample is distributed from the storage chamber to the reaction chambers via the distributing flow path by a suction provided by the sucking port;
- a liquid reservoir located between the reaction chambers and the receiving chamber; and
- an air tank for each of the reaction chambers and attached, and supplies oxygen, to each of the reaction chambers.

18. The testing device according to claim 17, which further comprises:
a second receiving chamber having a second sucking port and being in communication with the distributing flow path, wherein the liquid sample remaining in the distributing flow path is replaced by air and introduced into the second receiving chamber by a second suction provided by the second sucking port so as to make the reaction chambers independent from each other.

19. The testing device according to claim 17, which further comprises:
a through flow path connecting the distributing flow path and the sucking flow path, wherein the liquid sample remaining in the distributing flow path is replaced by air and introduced into the receiving chamber via the through flow path by a further suction provided by the sucking port so as to make the reaction chambers independent from each other.

20. The testing device according to claim 17, wherein the distributing flow path is branched prior to reaching the reaction chambers.

21. The testing device according to claim 17, wherein the transparent molded body is obtained by covering a plate substrate having a groove formed therein with a film or a resin plate, wherein one or more of the plate substrate, the film and the resin plate are transparent.

22. The testing device according to claim 21, wherein the film or the resin plate is composed of an organic material selected from the group consisting of a polyolefin resin, a polyethylene resin, a polypropylene resin, a silicon resin, an ethylene vinyl acetate copolymer resin, a polyvinyl chloride resin, a polyurethane resin, a polyvinyl butyral resin, a polyvinyl alcohol resin, a vinyl acetate resin, a phenolic resin, a urea resin, an epoxy resin, and a melamine resin.

23. The testing device according to claim 21, wherein the film or the resin plate is composed of an organic material selected from the group consisting of a polyolefin resin, a polyethylene resin, a polypropylene resin.

24. The testing device according to claim 21, wherein the plate substrate is composed of an organic material selected from the group consisting of a polyethylene resin, a polypropylene resin, an ethylene vinyl acetate copolymer resin, a polystyrene resin, an AS resin, an ABS resin, a methacryl resin, a polyvinyl chloride resin, a polyamide resin, a polycarbonate resin, a polyethylene terephthalate resin, a polybutylene terephthalate resin, a phenolic resin, a urea resin, an epoxy resin, a melamine resin, a cycloolefin resin, and an acrylic resin.

* * * * *